United States Patent [19]

Sasaki et al.

[11] 4,447,558

[45] May 8, 1984

[54] PROCESS FOR PRODUCING AN ANTIMONY CONTAINING METAL OXIDE CATALYST

[75] Inventors: Yutaka Sasaki; Yoshimi Nakamura, both of Kanagawa, Japan

[73] Assignee: Nitto Chemical Industry Co., Ltd., Tokyo, Japan

[21] Appl. No.: 397,723

[22] Filed: Jul. 13, 1982

[30] Foreign Application Priority Data

Jul. 13, 1981 [JP] Japan ................... 56-108175

[51] Int. Cl.$^3$ ................... B01J 27/02; B01J 27/14; B01J 21/02; B01J 27/24
[52] U.S. Cl. ................... 502/215; 502/211; 502/210; 502/202; 502/201
[58] Field of Search ................... 252/432, 435, 437, 438, 252/439

[56] References Cited

U.S. PATENT DOCUMENTS

| | | | |
|---|---|---|---|
| 4,049,575 | 9/1977 | Sasaki et al. | 252/437 X |
| 4,169,042 | 9/1979 | McKay | 252/439 X |
| 4,169,785 | 10/1979 | Eberly, Jr. | 252/439 |
| 4,280,928 | 7/1981 | Kirch et al. | 252/435 X |
| 4,316,856 | 2/1982 | Guttmann et al. | 252/437 X |
| 4,335,018 | 6/1982 | Franz et al. | 252/435 |
| 4,339,394 | 7/1982 | Grosseles et al. | 252/432 X |
| 4,374,758 | 2/1983 | Sasaki et al. | 252/439 |

Primary Examiner—Delbert E. Gantz
Assistant Examiner—William G. Wright
Attorney, Agent, or Firm—Sughrue, Mion, Zinn, Macpeak, and Seas

[57] ABSTRACT

A process for preparing an antimony-containing metal oxide catalyst, comprising the steps of calcining at about 500° to 1,000° C. a metal oxide composition containing, as essential elements, antimony and at least one element selected from the group consisting of iron, cobalt, nickel, manganese, uranium, tin and copper, impregnating the calcined oxide composition with a tellurium-containing solution, drying the impregnated composition, and calcining the dried composition at about 400° to 850° C., wherein the tellurium-containing impregnating solution is a homogeneous, stable solution containing tellurium and at least one element selected from the group consisting of molybdenum and tungsten.

Thus process is also useful for the modification of existing metal oxide catalyst of low performance and the reactivation of existing deteriorated metal oxide catalyst.

12 Claims, No Drawings

PROCESS FOR PRODUCING AN ANTIMONY CONTAINING METAL OXIDE CATALYST

FIELD OF THE INVENTION

The present invention relates to a process for preparing an antimony-containing metal oxide catalyst, and more particularly, it relates to a new process of preparing an antimony-containing metal oxide catalyst which is high in activity and suitable for oxidation, oxidative dehydrogenation, and ammoxidation of olefins.

BACKGROUND OF THE INVENTION

It is known that an antimony-containing metal oxide catalyst, more particularly, a catalyst composed of antimony oxide and an oxide of at least one kind of metal (simply referred to as a polyvalent metal hereinafter) selected from the group consisting of iron, cobalt, nickel, manganese, uranium, tin, and copper is useful for the production of unsaturated aldehydes through oxidation of olefins, the production of diolefins through oxidation dehydrogenation of olefins, and the production of unsaturated nitriles through ammoxidation of olefins. For instance, known catalysts are composed of antimony oxide and an oxide or iron, cobalt, or nickel, which is claimed as a catalyst to be useful for the production of acrylonitrile through ammoxidation of propylene in Japanese Patent Publication No. 19111/63. A catalyst composed of antimony oxide and iron oxide is also disclosed in U.S. Pat. No. 3,197,419. Another catalyst composed of antimony oxide and tin oxide is disclosed in U.S. Pat. No. 3,152,170, a catalyst composed of antimony oxide and uranium oxide is disclosed in U.S. Pat. No. 3,308,151, and a catalyst composed of antimony oxide and manganese or copper oxide is disclosed in U.S. Pat. Nos. 3,200,081 and 3,340,291.

However, these catalysts do not produce satisfactory yields of the intended product, and efforts have been made to improve their performance by adding other elements. For instance, there is disclosed in U.S. Pat. No. 3,668,147 a multiple accelerated antimony-polyvalent metal oxide catalyst in which a catalyst composed of antimony oxide and iron oxide, antimony oxide and tin oxide, or antimony oxide and uranium oxide, is incorporated with tellurium oxide and an oxide of at least one element selected from the group consisting of vanadium, molybdenum, and tungsten.

These antimony-containing metal oxide catalysts are prepared from compounds which become oxides after decomposition with heating. Usually, the raw materials for respective components are mixed and precipitated, and the precipitates are dried and calcined. However, this method does not invariably provide catalysts having preferred activity and properties because the activity and properties of the catalysts are greatly affected even by slight variation of the calcination temperature.

A solution to this problem was disclosed in U.S. Pat. No. 4,049,575. According to this disclosure, an antimony-containing metal oxide catalyst is prepared by calcining an antimony-polyvalent metal oxide composition that constitutes the catalyst matrix, impregnating the calcined composition with an aqueous solution containing tellurium and at least one element selected from the group consisting of molybdenum, vanadium, and tungsten, and drying and calcining the resulting composition. In preparation of catalysts by the impregnation method, it is very important to prepare a homogeneous, stable impregnant containing catalyst components in predetermined quantities. In this connection, the method disclosed in U.S. Pat. No. 4,049,575 involves industrial problems in the preparation of the impregnant containing tellurium and other additives.

In other words, the above-mentioned impregnating solution is prepared by dissolving metallic tellurium or a tellurium compound such as tellurium dioxide and tellurous acid in nitric acid, and then mixing the tellurium-containing nitric acid solution with a solution containing other components. This method is industrially feasible from the standpoint of operation and economy. In addition, this method is advantageous in that the catalyst components other than tellurium are comparatively high in solubility in the form of nitrate and they can be prepared in pure form with ease. Nevertheless, this method is not desirable because the tellurium-containing nitric acid solution tends to form a precipitate on addition of an aqueous solution of a water-soluble molybdenum compound such as ammonium metamolybdate and ammonium paramolybdate, or on addition of an aqueous solution of a water-soluble tungsten compound such as ammonium metatungstate and ammonium paratungstate, during the preparation of an impregnant containing both a tellurium component and a molybdenum component or tungsten component. Thus it has been impossible to prepare homogeneous, stable solutions in a broad range of concentrations. This is true particularly in the preparation of a tellurium-containing nitric acid solution which contains a tungsten component alone or a tungsten component and molybdenum component together. As mentioned above, it has been very difficult to prepare, by using a tellurium-containing nitric acid solution, a homogeneous, stable impregnant containing tellurium and molybdenum and/or tungsten.

Such an impregnant may be dispensable in a process in which a nitric acid solution of tellurium and an aqueous solution of ammonium molybdate or ammonium tungstate are used independently. According to such a process, the catalyst is prepared by impregnation in two steps. That is, the catalyst matrix is impregnated with a nitric acid solution of tellurium, followed by drying and calcining. The resulting composition is then impregnated with an aqueous solution of ammonium paratungstate, followed by drying and calcining. The steps may be inverted. A detail description is given later in Comparative Example 1-b. This process, however, requires complicated steps, and is not industrially feasible.

According to the process disclosed in U.S. Pat. No. 4,049,575, the homogeneous, stable impregnating solution is prepared by dissolving telluric acid and a water-soluble molybdenum compound in water. Telluric acid, however, is disadvantageous as a raw material for industrial catalysts because it is expensive due to the fact that it is produced and purified by many steps including oxidizing metallic tellurium with chloric acid or oxidizing tellurium dioxide with potassium permanganate. Furthermore, it has no broad area of industrial application. In addition, telluric acid of high purity is not readily available, presumably due to the nature of its production process.

U.S. Pat. No. 3,474,042 discloses a process for preparing a catalyst by impregnating a carrier such as silica and alumina with a homogeneous solution containing a tellurium component and a molybdenum or tungsten component. According to this disclosure, the tellurium component is prepared from telluric acid, the molybdenum component is prepared from a peroxymolybdenum compound obtained through the reaction of ammonium molybdate and hydrogen peroxide, and the tungsten component is prepared from a peroxytungsten compound obtained through the reaction of ammonium tungstate and hydrogen peroxide. This method is still industrially infeasible because expensive tellurium acid is used as a raw material of the tellurium component and safety problems are involved in the use of a large quantity of hydrogen peroxide for the preparation of a peroxymolybdenum compound and peroxytungsten compound.

In order to solve the aforesaid problems involved in preparing the impregnating solution containing tellurium and other components by using a nitric acid solution of tellurium, the present inventors carried out a series of researches which led to this invention. This invention relates to an improvement of U.S. Pat. No. 4,049,575 cited above.

SUMMARY OF THE INVENTION

It is an object of the present invention to provide a process for preparing a homogeneous, stable impregnating solution containing tellurium and molybdenum and/or tungsten together, by using nitric acid solutions of metallic tellurium, tellurium oxide, etc., which are easy and safe to handle on an industrial scale.

It is another object of this invention to provide a process for preparing an antimony-containing metal oxide catalyst of high activity from the aforesaid impregnating solution in an industrially advantageous manner.

In studies to achieve the above objectives, it was found that the nitric acid solution containing tellurium and molybdenum and/or tungsten together is homogeneous and stable and does not form any precipitate, if the solution is prepared from nitric acid of a specific concentration, a tellurium compound, and heteropoly acid of molybdenum or tungsten having phosphorus or silicon as a hetero element. It was further found that the solution can be made stable when the pH is adjusted to lower than 3. It was also found that the catalyst prepared from this solution is superior in performance. It was found that it is difficult to prepare a homogeneous, stable solution if other compounds other than mentioned above are used as the raw materials for molybdenum and tungsten. The present invention is based on these findings.

The gist of the present invention resides in a process for preparing an antimony-containing metal oxide catalyst by the steps of calcining at about 500° to 1,000° C. a metal oxide composition containing as essential elements antimony and at least one element selected from the group consisting of iron, cobalt, nickel, manganese, uranium, tin, and copper, impregnating the calcined oxide composition with a tellurium-containing solution, drying the impregnated composition, and finally calcining the dried composition at about 400° to 850° C. The resulting composition gives greatly improved results because as the tellurium-containing impregnating solution there is used a homogeneous, stable solution containing tellurium and molybdenum and/or tungsten. The solution contains a tellurium compound and at least one kind of heteropoly acid. The acid is selected from the group consisting of phosphomolybdic acid, silicomolybdic acid, phosphotungstic acid, and silicotungstic acid. The solution contains nitrate radicals in a concentration of at least 5 g/liter and has a pH lower than 3.

According to the process of this invention, as will be shown in the Examples given later, the tellurium-containing impregnating solution can be prepared without the problem that molybdenum or tungsten component is immiscible with the nitric acid solution of a tellurium compound. Thus it is possible to prepare a homogeneous, stable solution containing tellurium and molybdenum and/or tungsten together. Moreover, this solution is uniform and stable over a broad range of concentrations and ratios of tellurium and molybdenum and/or tungsten. The antimony-containing metal oxide catalyst prepared from such a solution has an extremely high activity. The raw materials for the tellurium, molybdenum, and tungsten components used for the preparation of the impregnating solution are readily available at reasonable prices as industrial products.

Therefore, the process of this invention permits one to produce with great industrial advantage the antimony-containing metal oxide catalyst useful for oxidation, oxidative hydrogenation, and ammoxidation of olefins.

The process of this invention is advantageous over the known process for preparing the catalyst by mixing catalyst components in that the antimony-containing metal oxide catalyst is only slightly dependent on the calcining temperature and has high activity and superior properties.

Another advantage of this invention is that it is possible to prepare the antimony-containing metal oxide catalyst of high performance with small quantities of tellurium, molybdenum, and tungsten components.

The high catalyst performance is achieved when a heteropoly acid of molybdenum and/or tungsten is used in the presence of nitrate radicals. When telluric acid is used as a raw material of tellurium, it is easy to prepare a comparatively stable impregnating solution. Even in such a case, a catalyst of higher performance can be obtained if nitric acid or nitrate radicals are present and the pH of the solution is adjusted to lower than 3.

The catalyst produced according to the process of this invention is not limited in composition, but the preferable composition is represented by the following empirical formula:

$$Me_aSb_bX_cP_dTe_eQ_fO_g(SiO_2)_h$$

where Me is at least one element selected from the group consisting of Fe, Co, Ni, Mn, U, Sn, and Cu; X is at least one element selected from the group consisting of Mo and W; Q is at least one element selected from the group consisting of Li, Na, K, Rb, Cs, Mg, Ca, Sr, Ba, La, Ce, Ti, Zr, V, Nb, Ta, Cr, Re, Ru, Os, Rh, Ir, Pd, Pt, Ag, Au, Zn, Cd, Hg, B, Al, Ga, In, Tl, Ge, Pb, As, and Bi; and subscripts a, b, c, d, e, f and g denote the atomic ratios as follows:
when
  a=10
  b=5 to 60 (preferably 5 to 30)
  c=0.01 to 5 (preferably 0.05 to 3)
  d=0 to 5 (preferably 0 to 3)
  e=0.01 to 10 (preferably 0.05 to 5)
  f=0 to 20 (preferably 0 to 10)
  g=a number corresponding to oxides formed by the combination of the above-mentioned components.
  h=0 to 200

The catalyst produced according to the process of this invention may be used without a carrier, but it should preferably be supported on a proper carrier. Examples of such carriers are silica, alumina, titania, zirconia, and silica-alumina. Preferable among them is silica. The quantity of the carrier to be used should be determined according to the desirable physical properties of the catalyst and the reaction rate required. In general, the quantity of the carrier should preferably be about 10 to 90% of the total weight of the catalyst.

The process of this invention is initiated by calcining an antimony-polyvalent metal oxide composition containing, as essential elements, antimony and at least one element selected from the group consisting of iron, cobalt, nickel, manganese, uranium, tin, and copper, at about 500° to 1,000° C. for about 1 to 50 hours. The calcination may be performed in a single stage at a fixed temperature or in two stages consisting of preliminary calcination and high-temperature calcination. Where calcination at high temperatures, say 700° C. or higher, is desirable, two-stage calcination is preferred. In such case, the preliminary calcination should preferably be carried out at about 200° to 600° C. The optimum calcination conditions vary with the catalyst composition. In the preferred mode of operation, the preliminary calcination at about 200° to 600° C. for about 1 to 50 hours is followed by the high-temperature calcination at about 600° to 1,000° C. for about 1 to 50 hours.

The antimony-polyvalent metal oxide composition which constitutes the matrix of the catalyst may contain vanadium, molybdenum, tungsten, tellurium, magnesium, calcium, lanthanum, cerium, titanium, zirconium, niobium, tantalum, chromium, silver, zinc, boron, aluminum, gallium, germanium, lead, phosphorus, arsenic, and bismuth. The antimony-polyvalent metal oxide composition may be prepared according to the processes disclosed in U.S. Pat. Nos. 3,668,147 and 4,049,575 cited above.

After calcination, the antimony-polyvalent metal oxide composition is subsequently impregnated with a homogeneous, stable solution containing tellurium and molybdenum and/or tungsten together.

The heteropoly acids used for preparing the impregnating solution are phosphomolybdic acid, silicomolybdic acid, phosphotungstic acid, and silicotungstic acid, represented by the following formulas. They are used as such or in the form of aqueous solution.

Phosphomolybdic acid: $H_3[PMo_{12}O_{40}] \cdot nH_2O$
Silicomolybdic acid: $H_4[SiMo_{12}O_{40}] \cdot nH_2O$
Phosphotungstic acid: $H_3[PW_{12}O_{40}] \cdot nH_2O$
Silicotungstic acid: $H_4[SiW_{12}O_{40}] \cdot nH_2O$ It is also possible to use the compositions having a structure similar to above in which Mo is partly replaced by V and/or W and W is partly replaced by V and/or Mo.

There are a large number of known heteropoly acids of the similar structure, but preferable ones for this invention are heteropoly acid of molybdenum or tungsten containing phosphorus or silicon as the hetero element. This applies to the case where the impregnating solution containing molybdenum and tungsten together is prepared. It will be difficult to prepare the homogeneous, stable solution if either of the molybdenum component or tungsten component is derived from other raw materials than the aforesaid heteropoly acids.

The aqueous solution of the heteropoly acid should be 1 to 50 wt% (as $MoO_3$ or $WO_3$) in concentration.

The tellurium compound used for preparation of the impregnating solution include metallic tellurium, tellurium monoxide, tellurium dioxide, tellurous acid, tellurium trioxide, and telluric acid of commercial technical grade.

The impregnating solution is prepared by dissolving simultaneously the aforesaid heteropoly acid and tellurium compound in nitric acid. The impregnating solution may also be prepared by dissolving a tellurium compound in nitric acid and then an aqueous solution of heteropoly acid or a heteropoly acid is mixed with or dissolved in the tellurium-containing nitric acid solution. The impregnating solution may be prepared at any temperature in the range from normal temperature to about 100° C.

The nitric acid should preferably contain nitrate radicals in a concentration of at least 5 g/liter. In the case of nitric acid thinner than this limit, a tetravalent tellurium compound hydrolyzes, resulting in an unstable solution, and a hexavalent tellurium compound such as telluric acid does not permit the resulting catalyst to exhibit its maximum performance. The preferred concentration of nitrate radicals is 10 to 1,000 g/liter.

Thus prepared impregnating solution containing tellurium and molybdenum and/or tungsten together is acid. It is desirable to adjust the impregnating solution to pH 3 or lower with nitric acid in order to keep the solution stable. If the pH is higher than this limit, a tetravalent tellurium compound tends to precipitate and the heteropoly acid is unstable.

The impregnating solution is homogeneous and stable over a broad range of concentrations of tellurium and molybdenum and/or tungsten.

The impregnating solution is compatible with other components, and may optionally contain a proper quantity of water-soluble compounds of various elements such as alkali metals, alkaline earth metals, rare earth elements, vanadium, niobium, tantalum, chromium, manganese, rhenium, iron, ruthenium, osmium, cobalt, rhodium, iridium, nickel, palladium, platinum, copper, silver, gold, zinc, cadmium, mercury, boron, aluminum, gallium, indium, thallium, germanium, tin, lead, phosphorus, arsenic, and bismuth. These compounds should preferably be used in the form of nitrate. Ammonium ions should be avoided as far as possible because they impair the stability of the solution.

The calcined antimony-polyvalent metal oxide composition may be impregnated with the aforesaid tellurium-containing impregnating solution by any method. An easy-to-perform method comprises the steps of measuring the volume of pores of the antimony-polyvalent metal oxide in the composition, preparing the impregnating solution containing tellurium of proper concentration and volume that correspond to the volume of the pores, and mixing well the composition (catalyst matrix) and the impregnating solution. This method is particularly preferred where the catalyst is used for the fluidized bed. None of the components in the impregnating solution prepared as above are selectively adsorbed on the calcined antimony-polyvalent metal oxide composition. Therefore, all the impregnating components are uniformly distributed in the finished catalyst.

Satisfactory impregnation is accomplished by mixing the catalyst matrix and the impregnating solution completely for about 10 minutes to 2 hours. A satisfactory effect is produced with the impregnated components (as oxides) in an amount less than 10 wt% in total, usually less than 5 wt% in total, based on the catalyst matrix. The preferred atomic ratio of the components to be impregnated is 1:0.01 to 5:0 to 5 for Te:(Mo, W):(alkali metals, alkaline earth metals, rare earth elements, V, Nb, Ta, Cr, Mn, Re, Fe, Ru, Os, Co, Rh, Ir, Ni, Pd, Pt, Cu, Ag, Au, Zn, Cd, Hg, B, Al, Ga, In, Tl, Ge, Sn, Pb, P, As, Bi).

After impregnation, the composition is dried and calcined at about 400° to 850° C. The optimum calcining conditions vary with the type and quantity of the components added. Calcining at about 400° to 850° C. for about 0.5 to 50 hours will be satisfactory. No stringent controls are required because the calcining conditions only slightly affects the activity and physical properties of the resulting catalyst.

No elucidation has been made yet for the reaction between the antimony-polyvalent metal oxide composition and the components in the impregnating solution. It is considered that tellurium, molybdenum, and tungsten components react easily with the antimony-polyvalent metal oxide composition when calcining is performed.

The process of this invention may be applied to the modification of existing multiple accelerated antimony-polyvalent metal oxide catalysts, or to the reactivation of existing multiple accelerated antimony-polyvalent metal oxide catalysts which have deteriorated in activity due to reduction or decrease (or release) of catalyst components that took place during use for some reason or other.

Thus another embodiment of this invention consists in a process for preparing an antimony-containing metal oxide catalyst by the steps of impregnating a metal oxide catalyst containing as essential elements antimony and at least one element selected from the group consisting of iron, cobalt, nickel, manganese, uranium, tin, and copper and as additive components tellurium alone or the combination of tellurium and at least one kind of element selected from the group consisting of vanadium, molybdenum and tungsten, which has deteriorated in activity due to reduction or decrease (or release) of the additive components, with a tellurium-containing solution, drying the impregnated catalyst composition, and finally calcining the dried catalyst composition at about 400° to 850° C. The process is greatly improved by using as the tellurium-containing impregnating solution, a homogeneous, stable solution containing tellurium and molybdenum and/or tungsten. The solution contains a tellurium compound and at least one kind of heteropoly acid. The heteropoly acid is selected from the group consisting of phosphomolybdic acid, silicomolybdic acid, phosphotungstic acid, and silicotungstic acid. The solution contains nitrate radicals in a concentration of at least 5 g/liter and has a pH lower than 3.

This embodiment is carried out in the same way as the first embodiment mentioned above, except that the first calcining step is omitted.

The process of this invention is industrially advantageous because it produces invariably and easily multiple accelerated antimony-polyvalent metal oxide catalysts having high activity and superior physical properties. The process is also useful to modify or reactivate deteriorated oxide catalysts.

In what follows, the embodiments and advantages of this invention are described in detail with reference to Examples and Comparative Examples.

In this specification, the yield and selectivity of the end product are defined as follows:

Yield(%)=$A/B$×100 where

A: Weight of carbon in the end product produced,
B: Weight of carbon in the hydrocarbon that was supplied as a raw material.

Selectivity(%)=$A/C$×100 where

A: Weight of carbon in the end product produced,
C: Weight of carbon in the hydrocarbon as a raw material that reacted.

The contact time is defined as follows:

Contact time(sec)=$D/E$ where
D: Volume of packed catalyst (liter),
E: Flow rate of gas supplied (liter/sec).

Procedure for Activity Test (1)

In ammoxidation of propylene:

A fluidized bed reactor having a fluidizing section, 2 inches in inside diameter and 2 meters in height, is packed with 1,200 g to 1,800 g of a proper catalyst. To this reactor is fed a gas of the following composition at an apparent linear velocity of 15 cm/sec, and reaction is carried out at normal pressure.

Oxygen (supplied as air)/propylene=2.10 (molar ratio)
Ammonia/propylene=1.15 (molar ratio).

Procedure for Activity Test (2)

In oxidative dehydrogenation of butene-1:

25 ml of catalyst molded into 2 mm×2 mm $\phi$ cylinders is filled in a U-shaped fixed bed reactor, 16 mm in inside diameter and 500 mm in length. The reactor is kept at a predetermined temperature in a molten salt bath composed of equal quantities of sodium sulfite and potassium nitrate. Into this reactor is supplied a gas of the following composition at a rate of 7.5 liter/hour (N.T.P.), and reaction is carried out at normal pressure.

Oxygen (supplied as air)/butene-1=1.1 (molar ratio)
Water/butene-1=1.5 (molar ratio)

EXAMPLE 1

A catalyst matrix having an empirical formula Fe$_{10}$Sb$_{25}$O$_{65}$(SiO$_2$)$_{30}$ was prepared as follows:

Into 17.5 liters of nitric acid (s.g.: 1.38) heated to about 80° C. was slowly added 4.72 kg of metallic antimony powder. After antimony was oxidized completely, excess nitric acid was removed and antimony oxide was washed with water. The antimony oxide was pulverized in a ball mill for 3 hours. (Component I)

Into 6.25 liters of nitric acid (s.g.: 1.38) diluted with 7.75 liters of water and heated to about 80° C. was slowly added 0.865 kg of electrolytic iron powder which was dissolved completely. (Component II)

13.9 kg of 20% silica sol was weighed out. (Component III)

The above Components I, II and III were mixed, and the mixture was adjusted to pH 2 by adding slowly 15% aqueous ammonia with vigorous stirring. The resulting slurry was heated at 100° C. for 3 hours with stirring. The slurry underwent spray drying, and the resulting powder was calcined at 300° C. for 5 hours, at 500° C. for 2 hours, and finally at 850° C. for 2 hours in the written order.

On the other hand, 15.8 g of metallic tellurium powder was dissolved in 800 g of 45% nitric acid heated to 50° C. To this solution was added 18.0 g of aqueous solution of phosphotungstic acid (40 wt% as $WO_3$). The resulting solution containing tellurium and tungsten was a homogeneous, stable solution free of precipitate. This solution was diluted to 614 ml with pure water. The diluted solution was found to have a pH lower than 0 and the concentration of nitrate radicals was 520 g/liter.

The diluted solution was added to 2 kg of the previously prepared catalyst matrix (having a pore volume of 0.32 ml/g). After mixing for about 1 hour, the mixture was dried at 120° C. for 16 hours, and subsequently calcined at 400° C. for 4 hours and finally at 750° C. for 5 hours. The catalyst prepared in this manner was found to have an empirical formula of $W_{0.1}Te_{0.4}P_{0.01}Fe_{10}Sb_{25}O_{66.12}(SiO_2)_{30}$.

Comparative Example 1-a

An attempt was made to prepare a catalyst of the same composition as Example 1 in the same manner as in Example 1, except that ammonium paratungstate was used as the raw material for the tungsten component and phosphoric acid was used as the raw material for the phosphorus component. No homogeneous, stable solution containing tellurium and tungsten together was prepared from the nitric acid solution of metallic tellurium and the aqueous solution of ammonium paratungstate. The mixture formed precipitates under any mixing conditions. Thus the attempt was abandoned.

Comparative Example 1-b

Since it was found in above Comparative Example 1-a that it is impossible to prepare a homogeneous, stable solution containing tellurium and tungsten together from the nitric acid solution of metallic tellurium and the aqueous solution of ammonium paratungstate, a catalyst of the same composition as Example 1 was prepared according to the following two-stage impregnating method.

In 45% nitric acid heated to 50° C. was slowly dissolved 15.8 g of metallic tellurium, and this nitric acid solution was diluted to 614 ml with 45% nitric acid. The nitric acid solution was added to 2 kg of the catalyst matrix having an empirical formula of $Fe_{10}Sb_{25}O_{65}(SiO_2)_{30}$ prepared as in Example 1. After mixing for about 1 hour, the mixture was dried at 120° C. for 16 hours, and subsequently calcined at 400° C. for 4 hours.

On the other hand, 8.1 g of ammonium paratungstate was suspended in 600 ml of pure water and dissolved completely with heating to 70° C. To this solution was added 0.30 g of 85% phosphoric acid and diluted to 614 ml with pure water. The diluted solution was added to the previously prepared catalyst impregnated with the tellurium component, followed by mixing for about 1 hour. The mixture was dried at 120° C. for 16 hours, and calcined at 400° C. for 4 hours and finally at 750° C. for 5 hours in the written order. The catalyst prepared in this manner was found to have an empirical formula of $W_{0.1}Te_{0.4}P_{0.01}Fe_{10}Sb_{25}O_{66.12}(SiO_2)_{30}$.

Comparative Example 2

A catalyst having an empirical formula of $W_{0.25}Te_{1.0}Fe_{10}Sb_{25}O_{67.75}(SiO_2)_{30}$ was prepared as follows:

Into 7.2 liters of nitric acid (s.g.: 1.38) heated to about 80° C. was slowly added 1.95 kg of metallic antimony powder lower than 100 microns in particle diameter. After antimony was oxidized completely, excess nitric acid was removed and antimony oxide was washed five times, each time with 2 liters of water. The antimony oxide was pulverized in a ball mill for 3 hours. (Component I)

Into 3 liters of nitric acid (s.g.: 1.38) diluted with 4 liters of water and heated to about 80° C. was slowly added 0.358 kg of electrolytic iron powder and dissolved completely. Then 81.8 g of metallic tellurium powder (purity 99.9%) was added and dissolved. (Component II)

41.8 g of ammonium paratungstate was dissolved in 2 liters of water. (Component III)

3.84 kg of silica sol (containing 30 wt% of $SiO_2$) was weighed out. (Component IV)

The above Components I to IV were mixed, and the mixture was adjusted to pH 2 by adding slowly 15 wt% aqueous ammonia with vigorous stirring.

The resulting slurry was heated at 100° C. for 4 hours with vigorous stirring. The slurry underwent spray drying in the usual way, and the resulting fine spherical particles were calcined at 200° C. for 4 hours, at 400° C. for 4 hours, and finally at 800° C. for 8 hours, in the written order.

EXAMPLE 2-a

A catalyst matrix having an empirical formula of $W_{0.25}Te_{1.0}Fe_{10}Sb_{25}O_{67.75}(SiO_2)_{30}$ was prepared in the same manner as in Comparative Example 2.

In 45% nitric acid heated to 30° C. was dissolved completely 11.5 g of metallic tellurium powder. This nitric acid solution of tellurium was added to and mixed with 21.6 g of aqueous solution of phosphomolybdic acid (40 wt% as $MoO_3$). Thus prepared tellurium/molybdenum-containing solution was homogeneous and stable. This solution was diluted to 500 ml with pure water. The pH of this solution was lower than 0 and the concentration of nitrate radicals was 500 g/liter. This solution was added to 2 kg of the catalyst matrix (pore volume: 0.25 ml/g). After mixing for about 1 hour, the mixture was dried at 120° C. for 16 hours, and subsequently calcined at 400° C. for 4 hours and finally at 700° C. for 4 hours in the written order. The catalyst prepared in this manner was found to have an empirical formula of $Mo_{0.2}W_{0.25}Te_{1.3}P_{0.02}Fe_{10}Sb_{25}O_{67.39}(SiO_2)_{30}$.

EXAMPLE 2-b

A catalyst matrix having an empirical formula of $W_{0.25}Te_{1.0}Fe_{10}Sb_{25}O_{67.75}(SiO_2)_{30}$ was prepared in the same manner as in Example 2-a.

In 550 g of 45% nitric acid heated to 30° C. was dissolved completely 11.5 g of tellurium dioxide powder. This nitric acid solution containing tellurium was added to and mixed with 10.8 g of aqueous solution of phosphomolybdic acid (40 wt% as $MoO_3$) and 8.7 g of aqueous solution of silicotungstic acid (40wt% as $WO_3$). In this tellurium/molybdenum/tungsten-containing solution was dissolved 44.4 g of cupric nitrate $Cu(NO_3)_2 \cdot 6H_2O$. The tellurium/molybdenum/tungsten/copper-containing solution prepared in this manner was homogeneous and stable. This solution was diluted to 500 ml with pure water. The pH of this solution was lower than 0 and the concentration of nitrate radicals was 525 g/liter. This solution was added to 2 kg of the catalyst matrix (pore volume: 0.25 ml/g). After mixing for about 1 hour, the mixture was dried at 120° C. for 16 hours, and subsequently calcined at 400° C. for 4 hours and finally at 700° C. for 4 hours. The catalyst prepared in this manner was found to have an empirical formula of $Mo_{0.1}W_{0.3}Te_{1.3}P_{0.01}Cu_{0.5}Fe_{10}Sb_{25}O_{69.32}(SiO_2)_{30}$.

Comparative Example 3-a

A catalyst having an empirical formula of $W_{0.5}Mo_{1.2}Te_3B_1Co_4Fe_{10}Sb_{25}O_{81.6}(SiO_2)_{60}$ was prepared as follows:

5.84 kg of antimony trioxide powder was weighed out. (Component I)

Into 6.4 liters of nitric acid (s.g.: 1.38) diluted with 4 liters of water and heated was slowly added 0.894 kg of electrolytic iron powder and then was added 1.864 kg of cobalt nitrate. (Component II)

210 g of ammonium paratungstic acid was dissolved in 18.4 liters of water, and in this solution was dissolved 340 g of ammonium paramolybdate and then 1.104 kg of telluric acid (Component III)

In 19.22 kg of silica sol (containing 30 wt% of $SiO_2$) was dissolved 98 g of boric acid. (Component IV)

Components III, II and I were added to Component IV in the written order, and then 15% aqueous ammonia was added slowly with vigorous stirring to adjust the pH to 2. The resulting slurry underwent spray drying in the usual way, and the resulting fine spherical particles were calcined at 200° C. for 8 hours, at 400° C. for 16 hours. Two minutes later, one portion was calcined at 700° C. for 4 hours, and the remainder was calcined at 720° C. for 4 hours.

EXAMPLE 3-a

A catalyst having an empirical formula of $W_{0.2}Mo_{0.25}Te_{0.5}B_1Co_4Fe_{10}Sb_{25}O_{72.9}(SiO_2)_{60}$ was prepared as follows:

At first, a catalyst matrix having an empirical formula of $Mo_{0.25}B_1Co_4Fe_{10}Sb_{25}O_{71.29}(SiO_2)_{60}$ was prepared in the same manner as in Comparative Example 3-a, except that the W and Te components were not added and calcining was performed at 800° C. for 5 hours.

In 666 g of 40% nitric acid heated to 40° C. was dissolved 14.8 g of metallic tellurium powder by adding slowly. To this solution was added 35.9 g of aqueous solution of silicotungstic acid (30 wt% as $WO_3$). The tellurium/tungsten-containing solution prepared in this manner was homogeneous and stable. This solution was diluted to 0.62 liter with pure water. The pH of this solution was lower than 0 and the concentration of nitrate radicals was 390 g/liter. This impregnating solution was added to 2 kg of the catalyst matrix (pore volume: 0.31 ml/g), followed by mixing for 1.5 hours. The mixture was dried at 120° C. for 16 hours and calcined at 400° C. for 2 hours and finally at 720° C. for 4 hours in the written order.

EXAMPLE 3-b

At first, a catalyst matrix having an empirical formula of $Mo_{0.5}B_1CO_4Fe_{10}Sb_{25}O_{72.0}(SiO_2)_{60}$ was prepared in the same manner as in Comparative Example 3, except that the W and Te components were not added and calcining was performed at 820° C. for 4 hours.

In 80 g of 60% nitric acid heated was dissolved 8.8 g of copper chips with heating. The solution was diluted with 1.7 liters of pure water. In this diluted solution were dissolved 207 g of telluric acid and then 40.3 g of nickel nitrate. To this nitric acid solution of tellurium was added with mixing 80.4 g of aqueous solution of silicotungstic acid (40 wt% as $WO_3$). The tellurium/copper/nickel/tungsten-containing solution prepared in this manner was homogeneous and stable. This solution was diluted to 1.74 liters with pure water. The pH of this solution was lower than 0 and the concentration of nitrate radicals was 34 g/liter. This impregnating solution was added to 6 kg of the catalyst matrix (pore volume: 0.29 ml/g), followed by mixing for 1 hour. The mixture was dried at 120° C. for 16 hours and then calcined at 400° C. for 4 hours. The calcined product was divided into three portions, which were calcined at 680° C., 700° C., and 720° C., respectively, for 3 hours. The catalyst thus prepared was found to have an empirical formula of $W_{0.2}Mo_{0.5}Te_{1.3}B_1Cu_{0.2}Ni_{0.2}Co_4Fe_{10}Sb_{25}O_{75.60}(SiO_2)_{60}$.

Comparative Example 3-b

A catalyst of the same composition as that in Example 3-b was prepared in the same manner as in Comparative Example 3-a, except that calcining was performed at 700° C. for 4 hours and at 800° C. for 4 hours.

EXAMPLE 4

A catalyst matrix having an empirical formula of $Mo_{0.25}Te_{1.0}Cu_3Fe_{12}Sb_{25}O_{71.75}(SiO_2)_{60}$ was prepared in the following manner.

5.82 kg of antimony trioxide powder was weighed out. (Component I)

Into 7.1 liters of nitric acid (s.g.: 1.38) diluted with 9.0 liters of water and heated was slowly added 1.07 kg of electrolytic iron powder and then was added slowly 204 g of metallic tellurium powder. (Component II)

In 1 liter of water was dissolved 70.6 g of ammonium paramolybdate. (Component III)

28.84 kg of 20% silica sol was weighed out. (Component IV)

In 1 liter of water was dissolved 1,417 g of cupric nitrate $Cu(NO_3)_2.6H_2O$. (Component V)

Components II, V, I and III were added to Component IV in the written order, and then 15% aqueous ammonia was added dropwise to adjust the pH to 2, with stirring and heating at 100° C. for 4 hours.

The slurry prepared in this manner underwent spray drying in the usual way, and the resulting powder was calcined at 300° C. for 2 hours, at 500° C. for 2 hours, and finally at 820° C. for 4 hours in the written order.

This catalyst was filled in a fluidized bed reactor having the fluidizing section, 8 inches in inside diameter. This reactor was used for ammoxidation of propylene under the following test conditions.

Gas linear velocity: 18 cm/sec
Reaction pressure: 0.5 kg/cm$^2$G
Composition of gas to be supplied:
  Oxygen (supplied as air)/propylene = 1.9 (molar ratio),
  Ammonia/propylene = 1.0 (molar ratio).

The yield of acrylonitrile was 74% at the beginning of ammoxidation, but it decreased to 70% after ammoxidation at 450° C. for 200 hours.

The deteriorated catalyst (2 kg) was extracted from the reactor, and reactivated as follows:

In 310 g of 45% nitric acid heated to 30° C. was dissolved 8.7 g of metallic tellurium powder. To this solution was added 13.1 g of aqueous solution of phosphotungstic acid (40 wt% as $WO_3$), whereby the tellurium/tungsten-containing solution was prepared. This solution was homogeneous and stable. This solution was diluted to 560 ml with pure water. The pH of this solution was lower than 0 and the concentration of nitrate radicals was 230 g/liter. This impregnating solution was added to 2 kg of the aforesaid deteriorated catalyst (pore volume: 0.28 ml/g), followed by complete mixing for about 1 hour. The mixture was dried at 120° C. for 16 hours, and calcined at 400° C. for 4 hours and finally at 720° C. for 2 hours in the written order. The catalyst prepared in this manner was found to have an empirical formula of $Mo_{0.25}W_{0.1}Te_{1.3}P_{0.008}Cu_3Fe_{12}Sb_{25}O_{74.67}(SiO_2)_{60}$.

The catalysts prepared in the above Examples and Comparative Examples were subjected to an activity test according to the procedure for activity test (1). The results are shown in Table 1.

(2) Comparison between Examples 2-a and 2-b and Comparative Example 2

The catalyst, as in Comparative Example 2, which was prepared by the known process of mixing catalyst components exhibited the performance as shown in Table 1.

In Examples 2-a and 2-b, studies were made of the possibility of improving the catalyst of Comparative

TABLE 1

| Ex. No. | Composition of Catalyst (atomic ratio) | Method for Preparation of Catalyst | Calcining Conditions Temp. (°C.) | Calcining Conditions Time (hrs) | Test Condition Reaction Temp. (°C.) | Test Condition Contact Time (sec) | Yield of Acrylonitrile (%) | Conversion Rate of Propylene (%) | Selectivity of Acrylonitrile (%) |
|---|---|---|---|---|---|---|---|---|---|
| Ex. 1 | $W_{0.1}Te_{0.4}P_{0.01}Fe_{10}Sb_{25}O_{66.12}(SiO_2)_{30}$ | A | 750 | 5 | 470 | 4.0 | 82.4 | 99.1 | 83.1 |
| Comp. Ex. 1-b | Same composition as in Ex. 1. | B | 750 | 5 | 470 | 4.0 | 78.7 | 99.2 | 79.3 |
| Ex. 2-a | $Mo_{0.2}W_{0.25}Te_{1.3}P_{0.02}Fe_{10}Sb_{25}O_{67.39}(SiO_2)_{30}$ | A | 700 | 4 | 450 | 3.5 | 81.2 | 98.0 | 82.9 |
| Ex. 2-b | $Mo_{0.1}W_{0.3}Te_{1.3}P_{0.01}Cu_{0.5}Fe_{10}Sb_{25}O_{69.32}(SiO_2)_{30}$ | A | 720 | 2 | 450 | 3.5 | 82.1 | 99.0 | 82.9 |
| Comp. Ex. 2 | $W_{0.25}Te_{1.0}Fe_{10}Sb_{25}O_{67.75}(SiO_2)_{30}$ | C | 800 | 8 | 470 | 4.5 | 79.8 | 97.5 | 81.8 |
| Ex. 3-a | $W_{0.2}Mo_{0.25}Te_{0.5}B_1Co_4Fe_{10}Sb_{25}O_{72.9}(SiO_2)_{60}$ | A | 720 | 4 | 450 | 3.0 | 84.0 | 97.9 | 85.8 |
| Ex. 3-b | $W_{0.2}Mo_{0.5}Te_{1.3}B_1Cu_{0.2}Ni_{0.2}Co_4Fe_{10}Sb_{25}O_{75.60}(SiO_2)_{60}$ | | 680 | 4 | 450 | 3.5 | 84.3 | 98.2 | 85.8 |
| | | A | 700 | 4 | 450 | 3.5 | 84.4 | 98.0 | 86.1 |
| | | | 720 | 4 | 450 | 3.5 | 84.2 | 98.0 | 85.9 |
| Comp. Ex. 3-a | $W_{0.5}Mo_{1.2}Te_3B_1Co_4Fe_{10}Sb_{25}O_{81.6}(SiO_2)_{60}$ | C | 700 | 4 | 450 | 3.5 | 83.2 | 98.1 | 84.8 |
| | | | 720 | 4 | 450 | 4.0 | 79.3 | 98.3 | 80.1 |
| Comp. Ex. 3-b | Same composition as in Ex. 3-b. | C | 700 | 4 | 450 | 3.5 | | 4* | |
| | | | 800 | 4 | 450 | 3.5 | 77.5 | 94.6 | 81.9 |
| Ex. 4 | $Mo_{0.25}Te_{1.0}Cu_3Fe_{12}Sb_{25}O_{71.75}(SiO_2)_{60}\{2*^{1*}$ | C | 820 | 4 | 460 | 3.5 | 79.2 | 98.6 | 80.3 |
| | | | | | 460 | 3.5 | 75.0 | 95.7 | 78.4 |
| | $Mo_{0.25}W_{0.1}Te_{1.3}P_{0.008}Cu_3Fe_{12}Sb_{25}O_{74.67}(SiO_2)_{60}{}^{3*}$ | A | 720 | 2 | 455 | 3.5 | 80.8 | 99.0 | 81.6 |

Note:
A, B and C show Impregnation, Two-stage impregnation and Mixing, respectively.
1*means "Before deterioration"
2*means "After deterioration"
3*means "after impregnation"
4*means a large amount of carbon dioxide gas; low yield of acrylonitrile; and great change with time.

EXPLANATION OF EXAMPLES 1 TO 4 AND COMPARATIVE EXAMPLES 1 to 3

(1) Comparison between Example 1 and Comparative Examples 1-a and 1-b

In Example 1, a homogeneous, stable solution containing tellurium and tungsten together was prepared according to the process of this invention. The catalyst prepared using this solution exhibited good performance.

In Comparative Example 1-a, it was impossible to prepare a homogeneous, stable solution containing tellurium and tungsten together from ammonium paratungstate and a nitric acid solution containing tellurium prepared by dissolving metallic tellurium in nitric acid.

In Comparative Example 1-b, which was intended to eliminate the drawback in Comparative Example 1-a, the catalyst of the same composition as in Example 1 was prepared by the two-stage impregnating method, in which the catalyst matrix was impregnated with the solution prepared by dissolving metallic tellurium in nitric acid, followed by drying and calcining, and the resulting product was impregnated again with an aqueous solution of ammonium paratungstate, followed by drying and calcining. This method is apparently more complex than that in Example 1 and the resulting catalyst is inferior in performance to that in Example 1.

Example 2 by the process of this invention.

It is to be noted that in Examples 2-a and 2-b, it was possible to improve the catalyst of Comparative Example 2 by impregnating a small quantity of tellurium, molybdenum and tungsten according to the process of this invention. In addition, the improvement of yield of acrylonitrile and the increase of reaction rate are apparent from Table 1.

(3) Comparison between Examples 3-a and 3-b and Comparative Examples 3-a and 3-b In Comparative Example 3-a, the catalyst was prepared according to a known process of mixing all the catalyst components. The resulting catalyst was good in activity as shown in Table 1.

The catalysts prepared in Examples 3-a and 3-b according to the process of this invention contain less than half as much Mo, W and Te as the catalyst prepared in Comparative Example 3-a. Nevertheless, they are superior in performance to that in Comparative Example 3-a. Generally speaking, the raw materials for tellurium, molybdenum, and tungsten components are comparatively expensive. According to the process of this invention, the catalysts of high performance can be obtained with less amounts of such expensive components. Thus the present invention is economically advantageous.

The catalyst in Comparative Example 3-b is the same in composition as that in Example 3-b, but it was prepared by a known method of mixing all the catalyst components at the beginning. When the catalyst was calcined at 700° C. for 4 hours as in Example 3-b, a large amount of carbon dioxide gas evolved and the resulting catalyst was low in the yield of acrylonitrile and changed greatly with time. Attempts to improve the yield of acrylonitrile by raising the calcining temperature were not successful; no higher yield than 77.5% was achieved even when the calcining temperature was raised to 800° C., and the reaction rate was low with the resulting catalyst. In conclusion, the catalyst in Comparative Example 3-b was inferior to that in Example 3-b.

The effect of calcining temperature on the catalyst performance was studied. In Comparative Example 3-a, the yield of acrylonitrile decreased when the calcining temperature was raised from 700° C. to 720° C. On the other hand, in Example 3-b, the calcining temperature was varied from 680° C. to 720° C. at intervals of 20° C., but no variation of performance was observed. Thus, according to the process of this invention, the catalyst performance is less dependent on the calcining temperature and this is advantageous in industrial production of catalysts.

(4) Example 4

Example 4 shows that it is possible to reactivate (regenerate) the deteriorated catalyst according to the process of this invention.

EXAMPLE 5

A catalyst having an empirical formula of $U_{10}Sb_{50}W_{0.1}Te_{0.5}Zn_{0.5}O_{128.5}(SiO_2)_{60}$ was prepared as follows:

60.9 g of metallic antimony powder (100 mesh) was added slowly to 50 ml of heated 63% nitric acid, with the evolution of a brown gas. After standing at room temperature for 16 hours, excess nitric acid was removed and the precipitate was washed three times with 100 ml of water. (Component I)

50.2 g of uranyl nitrate $UO_2(NO_3)_2.6H_2O$ was dissolved in 100 ml of water. (Component II)

180.3 g of silica sol (containing 20 wt% of $SiO_2$) was weighed out. (Component III)

The above Components I, II, and III were mixed and heated to dryness.

The dried product was crushed, and the crushed powder was calcined at 200° C. for 2 hours and then at 400° C. for 2 hours. The calcined powder was kneaded with water and molded into pellets (2 mm×2 mm $\phi$). The pellets were dried at 130° C. for 16 hours and then calcined at 800° C. for 5 hours.

1.15 g of telluric acid was dissolved in 30 ml of water, and to this solution was added 1.16 g of solution of phosphotungstic acid (20 wt% as $WO_3$). To this solution was further added 1.49 g of zinc nitrate $Zn(NO_3)_2.6H_2O$, and the total volume was diluted to 44 ml. The pH of this solution was 2.2, and the concentration of nitrate radicals was 14 g/liter. This impregnating solution was sprayed onto the catalyst matrix prepared as above, followed by drying at 120° C. for 16 hours, and calcining at 400° C. for 2 hours and finally at 720° C. for 4 hours.

EXAMPLE 6

A catalyst having an empirical formula of $Sn_{10}Sb_{60}W_{0.25}Te_{0.3}O_{141.4}(SiO_2)_{60}$ was prepared as follows:

121.8 g of metallic antimony powder (100 mesh) and 19.8 g of metallic tin powder (100 mesh) were added slowly to 720 ml of heated nitric acid (s.p.: 1.38), with the evolution of a brown gas. After standing at room temperature for 16 hours, excess nitric acid was removed and the precipitate was washed three times with 100 ml of water. (Component I)

300 g of silica sol (containing 20 wt% of $SiO_2$) was weighed out. (Component II)

The above Components I and II were mixed and heated to dryness.

The dried product was crushed, and the crushed powder was calcined at 200° C. for 2 hours and then at 400° C. for 2 hours. The calcined powder was kneaded with water and molded into pellets (2 mm×2 mm $\phi$). The pellets were dried at 130° C. for 16 hours and then calcined at 830° C. for 3 hours.

0.64 g of metallic tellurium was dissolved slowly in 40 g of 30% nitric acid heated to 50° C. To this solution was added 3.9 g of phosphotungstic acid (25 wt% as $WO_3$). Thus a solution containing tellurium and tungsten was prepared. This solution was homogeneous and stable, and the pH of this solution was lower than 0, and the concentration of nitrate radicals was 170 g/liter. This solution was diluted to 69 ml with pure water, and this diluted solution was impregnated into the catalyst matrix prepared as above, followed by drying at 120° C. for 16 hours, and calcining at 400° C. for 2 hours and finally at 700° C. for 4 hours.

The catalysts prepared in Examples 5 and 6 were subjected to the activity test according to the procedure for activity test (2). The results are shown in Table 2.

TABLE 2

| | | Calcining Conditions | | Test Condition Reaction | Test Results | | |
|---|---|---|---|---|---|---|---|
| Example No. | Composition of Catalyst (atomic ratio) | Temp. (°C.) | Time (hrs) | Temp. (°C.) | Yield of Butadiene (%) | Conversion Rate of Butene-1 (%) | Selectivity of Butadiene (%) |
| Example 5 | $U_{10}Sb_{50}W_{0.1}Te_{0.5}Zn_{0.5}O_{128.5}(SiO_2)_{60}$ | 720 | 4 | 420 | 84 | 75 | 89 |
| Example 6 | $Sn_{10}Sb_{60}W_{0.25}Te_{0.3}O_{141.4}(SiO_2)_{60}$ | 700 | 4 | 410 | 96 | 82 | 85 |

Note:
In Examples 5 and 6, the method for preparation of catalyst was impregnation method.

EXPLANATION OF EXAMPLES 5 AND 6

The catalyst containing as main components U and Sb in Example 5 and the catalyst containing as main components Sn and Sb in Example 6 were prepared according to the process of this invention. The thus obtained catalysts exhibited good performance, respectively.

On the other hand, for comparison, the catalyst was prepared by previously mixing the tellurium and tungsten components with the metal oxide composition, followed by drying and calcining without using the process of this invention. The performance of the prepared catalyst was greatly dependent on the calcining temperature as same as the Comparative Examples 3-a and 3-b.

While the invention has been described in detail and with reference to specific embodiments thereof, it will be apparent to one skilled in the art that various changes and modifications can be made therein without departing from the spirit and scope thereof.

What is claimed is:

1. A process for preparing an antimony-containing metal oxide catalyst, comprising the steps of:
   calcining at about 500° to 1,000° C. a metal oxide composition containing, as essential elements, antimony and at least one element selected from the group consisting of iron, cobalt, nickel, manganese, uranium, tin, and copper;
   impregnating the calcined oxide composition with a tellurium-containing solution;
   drying the impregnated composition; and
   calcining the dried composition at about 400° to 850° C., wherein the tellurium-containing impregnating solution is a homogeneous, stable solution containing tellurium and at least one element selected from the group consisting of molybdenum and tungsten, said solution containing a tellurium compound and at least one heteropoly acid selected from the group consisting of phosphomolybdic acid, silicomolybdic acid, phosphotungstic acid, and silicotungstic acid, and said solution containing nitrate radicals in concentration of at least 5 g/liter and having a pH lower than 3.

2. A process as claimed in claim 1, wherein the tellurium-containing impregnating solution is a homogeneous, stable solution containing tellurium and molybdenum and/or tungsten and at least one element selected from the group consisting of sodium, potassium, rubidium, cesium, magnesium, calcium, barium, lanthanum, cerium, zirconium, manganese, iron, cobalt, nickel, copper, silver, zinc, boron, aluminum, vanadium, germanium, tin, phosphorus, antimony, and bismuth.

3. A process as claimed in any of claims 1 or 2, wherein the effective components form eventually the catalysts represented by the following empirical formula:

$$Me_aSb_bX_cP_dTe_eQ_fO_g(SiO_2)_h$$

wherein Me is at least one element selected from the group consisting of Fe, Co, Ni, Mn, U, Sn, and Cu; X is at least one element selected from the group consisting of Mo and W; Q is at least one element selected from the group consisting of Li, Na, K, Rb, Cs, Mg, Ca, Sr, Ba, La, Ce, Ti, Zr, V, Nb, Ta, Cr, Re, Ru, Os, Rh, Ir, Pd, Pt, Ag, Au, Zn, Cd, Hg, B, Al, Ga, In, Tl, Ge, Pb, As, and Bi; and subscripts a, b, c, d, e, f and g denote the atomic ratios as follows:

when
a=10
b=5 to 60
c=0.01 to 5
d=0 to 5
e=0.01 to 10
f=0 to 20
g=a number corresponding to oxides formed by the combination of the above-mentioned components, and
h=0 to 200.

4. A process as claimed in claim 1, wherein the tellurium compound is at least one kind selected from the group consisting of metallic tellurium, tellurium monoxide, tellurium dioxide, tellurous acid, tellurium trioxide, and telluric acid.

5. A process as claimed in any of claims 1 or 2, wherein the calcined oxide composition contains at least one component selected from the group consisting of vanadium, molybdenum, tungsten, tellurium, magnesium, calcium, lanthanum, cerium, titanium, zirconium, niobium, tantalum, chromium, silver, zinc, boron, aluminum, gallium, germanium, lead, phosphorus, arsenic, and bismuth.

6. A process as claimed in any of claims 1 or 2, wherein the calcined oxide composition is supported on an inert carrier.

7. A process for preparing an antimony-containing metal oxide catalyst, comprising the steps of:
   impregnating a metal oxide catalyst containing, as essential elements, antimony and at least one element selected from the group consisting of iron, cobalt, nickel, manganese, uranium, tin, and copper and, as additive components, tellurium alone or the combination of tellurium and at least one element selected from the group consisting of vanadium, molybdenum, and tungsten, said catalyst having deteriorated activity due to reduction or decrease of the additive components with a tellurium-containing solution;
   drying the impregnated catalyst composition; and
   calcining the dried catalyst composition at about 400° to 850° C., wherein the tellurium-containing impregnating solution is a homogeneous, stable solution containing tellurium and at least one element selected from the molybdenum and tungsten, said solution containing a tellurium compound and at least one heteropoly acid selected from the group consisting of phosphomolybdic acid, silicomolybdic acid, phosphotungstic acid, and silicotungstic acid, and said solution containing nitrate radicals in concentration of at least 5 g/liter and having a pH lower than 3.

8. A process as claimed in claim 7, wherein the tellurium-containing impregnating solution is a homogeneous, stable solution containing tellurium and an element selected from the group consisting of molybdenum and tungsten and at least one element selected from the group consisting of sodium, potassium, rubidium, cesium, magnesium, calcium, barium, lanthanum, cerium, zirconium, manganese, iron, cobalt, nickel, copper, silver, zinc, boron, aluminum, vanadium, germanium, tin, phosphorus, antimony, and bismuth.

9. A process as claimed in any of claims 7 or 8, wherein the effective components form eventually the catalysts represented by the following empirical formula:

$$Me_aSb_bX_cP_dTe_eQ_fO_g(SiO_2)_h$$

wherein Me is at least one element selected from the group consisting of Fe, Co, Ni, Mn, U, Sn, and Cu; X is at least one element selected from the group consisting of Mo and W; Q is at least one element selected from the group consisting of Li, Na, K, Rb, Cs, Mg, Ca, Sr, Ba, La, Ce, Ti, Zr, V, Nb, Ta, Cr, Re, Ru, Os, Rh, Ir, Pd, Pt, Ag, Au, Zn, Cd, Hg, B, Al, Ga, In, Tl, Ge, Pb, As, and Bi; and subscripts a, b, c, d, e f and g denote the atomic ratios as follows:

when
- a=10
- b=5 to 60
- c=0.01 to 5
- d=0 to 5
- e=0.01 to 10
- f=0 to 20
- g=a number corresponding to oxides formed by the combination of the above-mentioned components, and
- h=0 to 200.

10. A process as claimed in claim 7, wherein the tellurium compound is at least one kind selected from the group consisting of metallic tellurium, tellurium monoxide, tellurium dioxide, tellurous acid, tellurium tiroxide, and telluric acid.

11. A process as claimed in any of claims 7, 8 or 10, wherein the calcined oxide composition contains at least one component selected from the group consisting of vanadium, molybdenum, tungsten, tellurium, magnesium, calcium, lanthanum, cerium, titanium, zirconium, niobium, tantalum, chromium, silver, zinc, boron, aluminum, gallium, germanium, lead, phosphorus, arsenic, and bismuch.

12. A process as claimed in any of claims 7, 8 or 10, wherein the calcined oxide composition is supported on an inert carrier.

* * * * *